US010405807B2

(12) United States Patent
Draeger et al.

(10) Patent No.: US 10,405,807 B2
(45) Date of Patent: *Sep. 10, 2019

(54) CONTACTLESS BLOOD PRESSURE MONITORING OF A PATIENT

(71) Applicant: International Business Machines Corporation, Armonk, NY (US)

(72) Inventors: David R. Draeger, Rochester, MN (US); Eric H. Jenney, Rochester, MN (US); John D. Vasquez, Big Bear Lake, CA (US)

(73) Assignee: International Business Machines Corporation, Armonk, NY (US)

(*) Notice: Subject to any disclaimer, the term of this patent is extended or adjusted under 35 U.S.C. 154(b) by 20 days.

This patent is subject to a terminal disclaimer.

(21) Appl. No.: 15/349,428

(22) Filed: Nov. 11, 2016

(65) Prior Publication Data

US 2018/0132795 A1    May 17, 2018

(51) Int. Cl.
*A61B 5/00* (2006.01)
*A61B 5/02* (2006.01)
(Continued)

(52) U.S. Cl.
CPC ............ *A61B 5/7278* (2013.01); *A61B 5/021* (2013.01); *A61B 5/0205* (2013.01); *A61B 5/02007* (2013.01); *A61B 5/0261* (2013.01); *A61B 5/02125* (2013.01); *A61B 5/1072* (2013.01); *A61B 5/1075* (2013.01); *A61B 5/1079* (2013.01); *A61B 5/742* (2013.01);
(Continued)

(58) Field of Classification Search
None
See application file for complete search history.

(56) References Cited

U.S. PATENT DOCUMENTS 5,193,548 A    3/1993  Miyawaki
5,598,842 A *  2/1997  Ishihara .............. A61B 5/0261
                                                           356/39
(Continued)

FOREIGN PATENT DOCUMENTS

CN    105011921 A    11/2015

OTHER PUBLICATIONS

Shiffman (Color, https://processing.org/tutorials/color/, Jun. 10, 2013).*
(Continued)

*Primary Examiner* — Carolyn A Pehlke
(74) *Attorney, Agent, or Firm* — Jason H. Sosa (57) ABSTRACT

Contactless blood pressure monitoring, includes: illuminating a blood vessel of a patient with infrared ('IR') light; receiving, by an IR camera through a polarizing filter, IR light reflected by the patient; capturing at a time based on a heartrate of the patient, a first IR image of the blood vessel of the patient when the blood vessel is distended; determining, from the first image, a maximum diameter of the blood vessel; capturing at a time based on the heartrate of the patient, a second IR image of the blood vessel of the patient when the blood vessel is contracted; determining, from the second IR image, a minimum diameter of the blood vessel; and calculating blood pressure of the patient in dependence upon the maximum and minimum diameters of the blood vessel.

18 Claims, 7 Drawing Sheets

(51) Int. Cl.
- A61B 5/021 (2006.01)
- A61B 5/026 (2006.01)
- A61B 5/0205 (2006.01)
- A61B 5/107 (2006.01)
- A61B 5/024 (2006.01)

(52) U.S. Cl.
CPC ........ *A61B 5/7475* (2013.01); *A61B 5/02416* (2013.01); *A61B 5/02433* (2013.01)

(56) References Cited

U.S. PATENT DOCUMENTS

| | | | |
|---|---|---|---|
| 9,622,666 B2* | 4/2017 | Pahlevan | A61B 8/4427 |
| 9,891,044 B2* | 2/2018 | Tu | G01B 21/00 |
| 2005/0228300 A1 | 10/2005 | Jaime et al. | |
| 2013/0079649 A1* | 3/2013 | Mestha | A61B 5/0022 600/508 |
| 2013/0218028 A1* | 8/2013 | Mestha | A61B 5/02125 600/479 |
| 2013/0322729 A1* | 12/2013 | Mestha | A61B 5/02 382/134 |
| 2014/0005554 A1 | 1/2014 | Das et al. | |
| 2015/0057511 A1 | 2/2015 | Basu | |
| 2015/0112214 A1* | 4/2015 | Mizukami | A61B 8/0891 600/490 |
| 2015/0216425 A1 | 8/2015 | Gladshtein et al. | |
| 2016/0033319 A1* | 2/2016 | Kovacs | G01G 19/44 177/25.13 |
| 2016/0106329 A1* | 4/2016 | Hoof | A61B 5/0261 600/479 |
| 2016/0262625 A1 | 9/2016 | Lawrenson et al. | |
| 2017/0049377 A1* | 2/2017 | Littell | A61B 5/0261 |

OTHER PUBLICATIONS

Zurek, Petr, Ondrej Krejcar, Marek Penhaker, Martin Cerny, and Robert Frischer. "Continuous noninvasive blood pressure measurement by near infra red CCD camera and pulse transmit time systems." In Computer Engineering and Applications (ICCEA), 2010 Second International Conference on, vol. 2, pp. 449-453. IEEE, 2010.*
Machine translation of Ding et al. (Chinese Pub. No. CN 105011921 A, Nov. 4, 2015).*
Braverman, Irwin M. "The cutaneous microcirculation." In Journal of Investigative Dermatology Symposium Proceedings, vol. 5, No. 1, pp. 3-9. Elsevier, 2000.*
Rogalski, A., P. Martyniuk, and M. Kopytko. "Challenges of small-pixel infrared detectors: a review." Reports on Progress in Physics 79, No. 4 (2016): 046501.*
Seal, Ayan, Suranjan Ganguly, Debotosh Bhattacharjee, Mita Nasipuri, and Dipak Kumar Basu. "A Comparative Study of Human thermal face recognition based on Haar wavelet transform (HWT) and Local Binary Pattern (LBP)." arXiv preprint arXiv:1309.1009 (2013).*
Soleimani, Effat, Manijhe Mokhtari-Dizaji, Nasser Fatouraee, and Hazhir Saberi. "Assessing the blood pressure waveform of the carotid artery using an ultrasound image processing method." Ultrasonography 36, No. 2 (2017): 144. Published online Sep. 20, 2016. doi: 10.14366/usg.16019.*
Chen, Hean C., Vinod Patel, Jutta Wiek, Salwan M. Rassam, and Eva M. Kohner. "Vessel diameter changes during the cardiac cycle." Eye 8, No. 1 (1994): 97.*
Auralife, *Instant Blood Pressure*, accessed Dec. 6, 2016 [online], 7 pages, URL: www.instantbloodpressure.com.
Wu et al., *Contactless and Cuffless Monitoring of Blood Pressure on a Chair Using E-Textile Materials*, Conference paper, 3rd IEEE/EMBS International Summer School on Medical Devices and Biosensors (abstract only), Oct. 2006, 1 page, ResearchGate.net [online], URL: www.researchgate.net/publication/224703767_Contactless_and_Cuffless_Monitoring_of_Blood_Pressure_on_a_ChairUsing_E-Textile_Materials.
Tarassenko et al., "Non-contact video-based vital sign monitoring using ambient light and auto-regressive models", Physiological Measurement, vol. 35, Mar. 28, 2014, pp. 807-831, Institute of Physics and Engineering in Medicine (online, iopscience.iop.org), URL: www.iopscience.iop.org/article/10.1088/0967-3334/35/5/807/pdf.
Chowdhury et al., "Noninvasive Cuffless Estimation of Blood Pressure using Photoplethesmography without Electrocardiograph Measurement", Conference Paper, IEEE Region 10 Technical Symposium, Apr. 2014, 3 pages, ResearchGate.org (online), URL: www.researchgate.net/publication/259579877_Noninvasive_Cuffless_Estimation_of_Blood_Pressure_using_Photoplethesmography_without_Electrocardiograph_Measurement.
Jeong, et al., "Introducing Contactless Blood Pressure Assessment Using a High Speed Video Camera", Journal of Medical Systems, Apr. 2016, vol. 40, Issue 4, (abstract only) 2 Pages, US National Library of Medicine, National Institutes of Health, National Center for Biotechnology Information online (PubMed.gov), URL: www.ncbi.nlm.nih.gov/pubmed/26791993.
Gu, et al., "A novel method for the contactless and continuous measurement of arterial blood pressure on a sleeping bed", Annual International Conference of the IEEE Engineering in Medicine and Biology Society, Sep. 2009, (abstract only) 1 Page, US National Library of Medicine, National Institutes of Health, National Center for Biotechnology Information online (PubMed.gov), URL: www.ncbi.nlm.nih.gov/pubmed/19965255.
Withings, "Wireless Blood Pressure Monitor for Apple and Android", amazon.com (online), [accessed Oct. 27, 2016], 2 pages, URL: https://www.amazon.com/Withings-Wireless-Pressure-Monitor-Android/dp/B00H43WOAK/ref=as_li_ss_tl?s=hpc&ie=UTF8&qid=1475264507&sr=1-1&keywords=withings+blood+pressure+cuff&linkCode=sl1&tag=lrh01-20&linkId=63adfc09cd648078279d459487e0b412.
Appendix P; List of IBM Patent or Applications Treated as Related, Aug. 1, 2017, 2 pages.
Fuksis, R. et al., "Infrared Imaging System for Analysis of Blood Vessel Structure", Institute of Electronics and Computer Science, Elektronika IR Elektrotechnika, Electronics and Electrical Engineering, vol. 1, No. 97, ISSN 1392-1215, Jan. 1, 2010, pp. 45-48.
International Search Report and Written Opinion, PCT/EP2017/062425, dated Sep. 1, 2017, 16 pages.

* cited by examiner

CONTACTLESS BLOOD PRESSURE MONITORING OF A PATIENT

BACKGROUND

Field of the Invention

The field of the invention is data processing, or, more specifically, methods, apparatus, and products for contactless blood pressure monitoring of a patient.

Description of Related Art

Current medical technology for gathering various blood related metrics such as blood pressure, heart rate, and blood flow rate, generally require physical contact between a patient and a medical device. For example, blood pressure is generally measured with a sphygmomanometer (also called a blood pressure meter or monitor) that includes an inflatable cuff. Such a cuff constricts the blood flow through a patient's veins when inflated and contracts in a controlled manner to measure the blood pressure of the vein when constricted and when unconstricted. Such a constriction may be uncomfortable for many patients.

SUMMARY

Methods, apparatus and products for A method of contactless blood pressure monitoring of a patient are disclosed in this specification. Such contactless blood pressure monitoring includes: illuminating, by a blood pressure monitoring system, a blood vessel of a patient with infrared ('IR') light; receiving, by an IR camera of the blood pressure monitoring system through a polarizing filter, IR light reflected by the patient; capturing at a time based on a heartrate of the patient, by the IR camera of the blood pressure monitoring system, a first IR image of the blood vessel of the patient when the blood vessel is distended; determining, by the blood pressure monitoring system from the first image, a maximum diameter of the blood vessel; capturing at a time based on the heartrate of the patient, by IR camera of the contactless blood pressure monitoring system, a second IR image of the blood vessel of the patient when the blood vessel is contracted; determining, by the blood pressure monitoring system from the second IR image, a minimum diameter of the blood vessel; and calculating, by the blood pressure monitoring system, blood pressure of the patient in dependence upon the maximum and minimum diameters of the blood vessel.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

Figure 1:
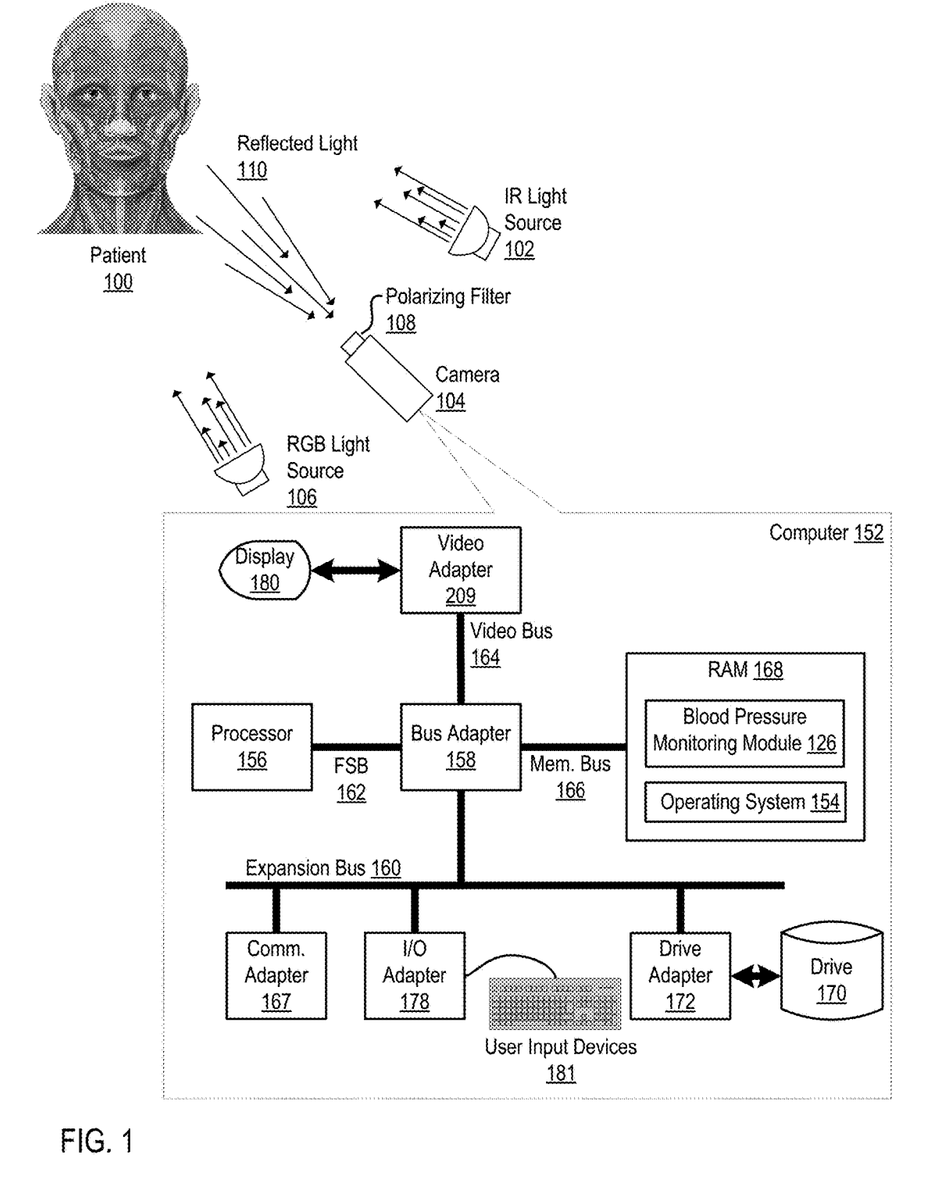
FIG. 1 sets forth a block diagram of a system configured for contactless blood pressure monitoring of a patient according to embodiments of the present invention.

Exemplary methods, apparatus, and products for contactless blood pressure monitoring of a patient in accordance with the present invention are described with reference to the accompanying drawings, beginning with FIG. 1. FIG. 1 sets forth a block diagram of a system configured for contactless blood pressure monitoring of a patient according to embodiments of the present invention. The system of FIG. 1 includes an example of a contactless blood pressure monitoring system according to various embodiments of the present invention. Such a blood pressure monitoring system may be implemented with automated computing machinery in the form of a computer (152), a camera (104), and a several light sources (106, 102).

The example computer (152) of FIG. 1 includes at least one computer processor (156) or 'CPU' as well as random access memory (168) ('RAM') which is connected through a high speed memory bus (166) and bus adapter (158) to processor (156) and to other components of the computer (152).

Stored in RAM (168) is a blood pressure monitoring module (126), a module of computer program instructions for contactless blood pressure monitoring in accordance with embodiments of the present invention. To that end, the blood pressure monitoring module (126) may illuminate, through use of the IR light source (102), one or more blood vessels of a patient (100) with IR light. In some embodiments of the present invention, illuminating the patient (100) with IR light may include illuminating the patient's face. The face includes many blood vessels in the form of veins, capillaries, and so on as will occur to readers of skill in the art. A blood vessel, as the term is used in this specification, may refer to any or all of: a vein, a capillary, and an artery.

The blood pressure monitoring module (126) may also receive, by an IR camera (104) through a polarizing filter (108), IR light reflected (110) by the patient (100). The camera (104) in the example of FIG. 1 may be implemented in a variety of ways. For example, the camera may be a digital video camera configured to capture IR light, visible light, or both. In some embodiments, multiple cameras may be implemented. In such an embodiment, one camera may be an RGBa camera and another an IR camera. A polarizing filter generally blocks polarized light from passing through the filter. Various types of polarizing filters maybe utilized in the example system of FIG. 1 such as a linear polarizer, a circular polarizer, or a combination of the two.

The blood pressure monitoring module (126), through the camera (104) may also capture at a time based on a heartrate of the patient a first IR image of the blood vessel of the patient when the blood vessel is distended—that is, fully dilated. Readers of skill in the art will recognize that such a 'capture' of an image may be carried out by capturing many images, by capturing a stream of frames in a digital video for example, and sampling the image data from the many images. In fact, each time the term 'capture' is used in this specification, readers of skill in the art will recognize that the term may refer to capturing many images and sampling the image data from those images.

A heart beat occurs in a cardiac cycle. The cardiac cycle begins in systole in which the ventricles of the heart contract, pumping blood out to the cardiovascular network. The cycle continues with an intervening pause, finally followed by diastole in which the ventricles of the heart relax. Responsive to the systole period in the cardiac cycle vessels experience increased pressure and thus distend. At this point, based on a known or calculated heart rate (described below), the blood pressure monitoring module captures an IR image of the blood vessel. Readers of skill in the art will recognize that capturing an IR image of a blood vessel refers generally to capturing an image of a portion of the vessel, rather than the entire vessel.

From the first IR image, the blood pressure monitoring module (126) may determine a maximum diameter of the blood vessel. The diameter may be calculated based on image processing of the image where edges of the vessels may be identified and the distance between the edges at the point of maximum distension may be calculated in a variety of ways.

The blood pressure monitoring module (126), through the camera (104), may then capture at a time based on the heartrate of the patient, a second IR image of the blood vessel of the patient when the blood vessel is contracted. The same portion of the blood vessel previously captured in an IR image when at full distension may be captured when the vessel is fully contracted, that is during the diastole period of the cardiac cycle of the heart. Likewise, the blood pressure monitoring may determine, from the second IR image, a minimum diameter of the blood vessel.

From these maximum diameters, the blood pressure monitoring module may then calculate blood pressure of the patient. Blood pressure is generally directly proportional to the product of the blood flow rate and total peripheral resistance. Total peripheral resistance is highly variable based on the radius of the blood vessel. The blood pressure monitoring module (126) may calculate blood pressure in a variety of ways. Blood pressure generally is measured at diastole and at systole. In some embodiments, the blood pressure monitoring module (126) may calculate the diastolic blood pressure by assuming or calculating a blood flow rate, approximating the total peripheral resistance based on the maximum diameter, and calculating the product of the two. The blood pressure monitoring module (126) may also calculate the systolic blood pressure by assuming or calculating a blood flow rate, approximating the total peripheral resistance based on the minimum diameter, and calculating the product of the two. Readers of skill in the art will recognize that this is but one way, among many possible ways, to calculate blood pressure from the maximum and minimum diameters of a blood vessel. Each such possible way is well within the scope of the present invention.

Readers of skill in the art will recognize the blood pressure monitoring system depicted in FIG. 1, including the computer (152), the camera (104), and the light sources (102, 106) may be implemented in a variety of different manners. The system may be implemented in a kiosk in which a user may approach the kiosk, request blood pressure monitoring through use of user input devices, and receive on a display (180) the results of the monitoring. Readers will also recognize that such monitoring may be dynamic and continuous. Many cameras, for example, may be configured to capture 24 frames each second, and the capture of IR images followed, determination of maximum and minimum vessel diameters, and calculation of blood pressure may be carried out many times in a short period of time.

Also stored in RAM (168) is an operating system (154). Operating systems useful in computers configured for contactless blood pressure monitoring of a patient according to embodiments of the present invention include UNIX™, Linux™, Microsoft Windows™, AIX™, IBM's i™ operating system, and others as will occur to those of skill in the art. The operating system (154) and blood pressure monitoring module (126) in the example of FIG. 1 are shown in RAM (168), but many components of such software typically are stored in non-volatile memory also, such as, for example, on a disk drive (170).

The computer (152) of FIG. 1 includes disk drive adapter (172) coupled through expansion bus (160) and bus adapter (158) to processor (156) and other components of the computer (152). Disk drive adapter (172) connects non-volatile data storage to the computer (152) in the form of disk drive (170). Disk drive adapters useful in computers configured for contactless blood pressure monitoring of a patient according to embodiments of the present invention include Integrated Drive Electronics ('IDE') adapters, Small Computer System Interface ('SCSI') adapters, and others as will occur to those of skill in the art. Non-volatile computer memory also may be implemented for as an optical disk drive, electrically erasable programmable read-only memory (so-called 'EEPROM' or 'Flash' memory), RAM drives, and so on, as will occur to those of skill in the art.

The example computer (152) of FIG. 1 includes one or more input/output ('I/O') adapters (178). I/O adapters implement user-oriented input/output through, for example, software drivers and computer hardware for controlling output to display devices such as computer display screens, as well as user input from user input devices (181) such as keyboards and mice. The example computer (152) of FIG. 1 includes a video adapter (209), which is an example of an I/O adapter specially designed for graphic output to a display device (180) such as a display screen or computer monitor. Video adapter (209) is connected to processor (156) through a high speed video bus (164), bus adapter (158), and the front side bus (162), which is also a high speed bus.

The exemplary computer (152) of FIG. 1 includes a communications adapter (167) for data communications with other computers and for data communications with a data communications network (not shown here). Such data communications may be carried out serially through RS-232 connections, through external buses such as a Universal Serial Bus ('USB'), through data communications networks such as IP data communications networks, and in other ways as will occur to those of skill in the art. Communications adapters implement the hardware level of data communications through which one computer sends data communications to another computer, directly or through a data communications network. Examples of communications adapters useful in computers configured for contactless blood pressure monitoring of a patient according to embodiments of the present invention include modems for wired dial-up communications, Ethernet (IEEE 802.3) adapters for wired data communications, and 802.11 adapters for wireless data communications.

The arrangement of computer components, cameras, and light sources making up the exemplary system illustrated in FIG. 1 are for explanation, not for limitation. Data processing systems useful according to various embodiments of the present invention may include additional servers, routers, other devices, and peer-to-peer architectures, not shown in FIG. 1, as will occur to those of skill in the art. Networks in such data processing systems may support many data communications protocols, including for example TCP (Transmission Control Protocol), IP (Internet Protocol), HTTP (HyperText Transfer Protocol), WAP (Wireless Access Protocol), HDTP (Handheld Device Transport Protocol), and others as will occur to those of skill in the art. Various embodiments of the present invention may be implemented on a variety of hardware platforms in addition to those illustrated in FIG. 1.

Figure 2:
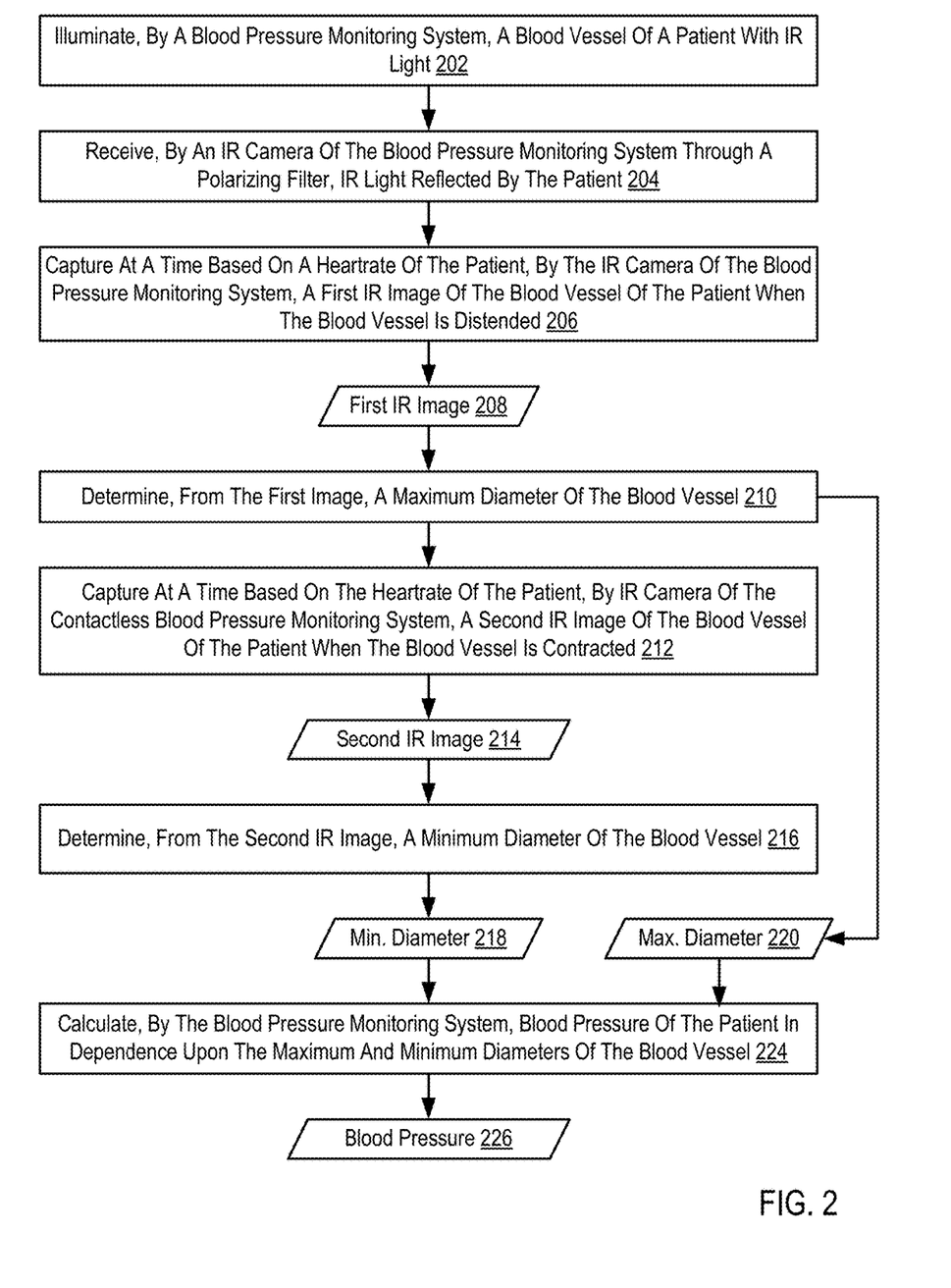
FIG. 2 sets forth a flow chart illustrating an exemplary method for contactless blood pressure monitoring of a patient according to embodiments of the present invention.

For further explanation, FIG. 2 sets forth a flow chart illustrating an exemplary method for contactless blood pressure monitoring of a patient according to embodiments of the present invention. The example method of FIG. 2 may be carried out by a system similar to that depicted in the example of FIG. 1.

The method of FIG. 2 includes illuminating (202), by a blood pressure monitoring system, a blood vessel of a patient with IR light. Illuminating (202) a blood vessel (or many blood vessels) may be carried out by projecting IR light, from an IR light source, on the face or other exposed skin of a patient.

The method of FIG. 2 also includes receiving (204), by an IR camera of the blood pressure monitoring system through a polarizing filter, IR light reflected by the patient. The IR camera may include one or more lens filters to block incoming light in the visible light spectrum while allowing IR light to reach a CCD (charged-couple device) sensor or CMOS (complementary metal oxide semiconductor) sensor.

The method of FIG. 2 also includes capturing (206) at a time based on a heartrate of the patient, by the IR camera of the blood pressure monitoring system, a first IR image (208) of the blood vessel of the patient when the blood vessel is distended. In an embodiment when the IR camera is a 24 FPS (frame per second) digital video camera, capturing a first IR image may be carried out by storing a stream of frames for a period of time and identifying one, based on the heartrate, that includes the vessel at full distension.

The method of FIG. 2 also includes determining (210), by the blood pressure monitoring system from the first image (208), a maximum diameter (220) of the blood vessel. The diameter may be calculated through image processing in which edge detection is employed to identify the edges of the vessel. The distance between two points on opposite detected edges may be determined as the diameter.

The method of FIG. 2 also includes capturing (212) at a time based on the heartrate of the patient, by IR camera of the contactless blood pressure monitoring system, a second IR image (214) of the blood vessel of the patient when the blood vessel is contracted. The method of FIG. 2 also includes determining, by the blood pressure monitoring system from the second IR image, a minimum diameter (218) of the blood vessel.

The method of FIG. 2 also includes calculating (224), by the blood pressure monitoring system, blood pressure of the patient in dependence upon the maximum and minimum diameters of the blood vessel. Calculating (224) blood pressure may be carried out by calculating both a diastolic and a systolic pressure and such calculation may be carried out in a variety of ways. In some embodiments, each diameter (220, 218) may be used to determine or assume a total peripheral resistance. With a known or calculated blood flow rate, calculating diastolic and systolic blood pressure may be carried out by determining the product of the total peripheral resistance (at each diameter) and the blood flow rate. After calculation, the blood pressure may be displayed or otherwise provided to the patient or electronically provided (via email, or other messaging) to a physician.

Figure 3:
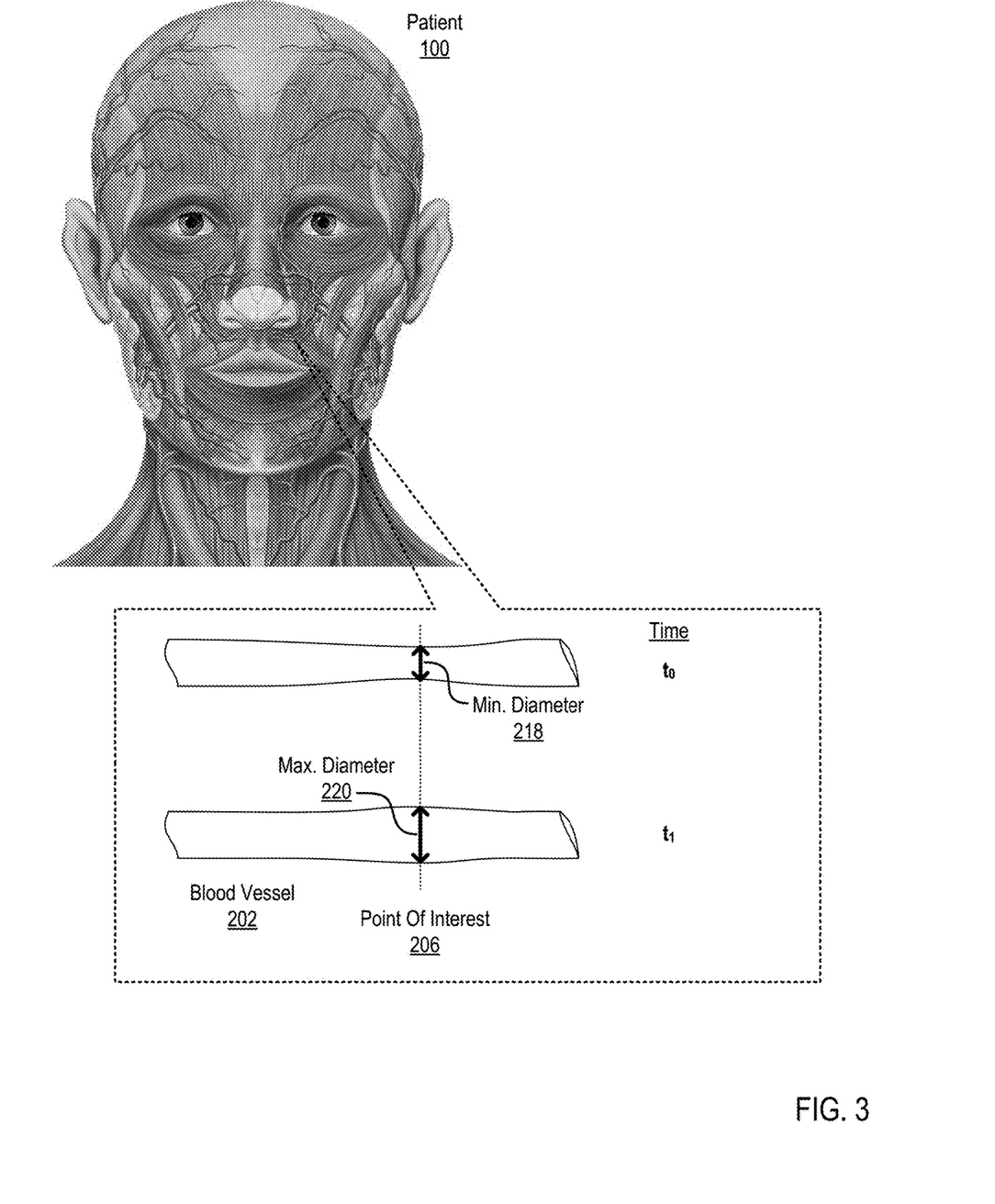
FIG. 3 sets forth a diagram of a blood vessel of a patient.

For further explanation, FIG. 3 sets forth a diagram of a blood vessel of a patient. One vessel (202) of the patient is blown up for clarity. The vessel is shown at two times: $t_0$ in which the heart is a diastole period and the vessel is contracting and $t_1$ in which the heart is in the systole period and the vessel is distended. At each time, while the patient is illuminated with IR light, the blood pressure monitoring system may capture an IR image that includes a point of interest (206). From the images the blood pressure monitoring system may determine, at the point of interest at $t_0$, the minimum (218) diameter and at the point of interest at $t_1$, the maximum diameter (220).

As mentioned above, the heartrate of the patient, which may be used to determine the timing of capturing the IR images of the patient's blood vessel at distension and contraction, may be assumed or otherwise calculated. To that end, the method of FIG. 4 sets forth a flow chart illustrating a further exemplary method for contactless blood pressure monitoring of a patient according to embodiments of the present invention that includes calculating the heartrate of the patient.

Figure 4:
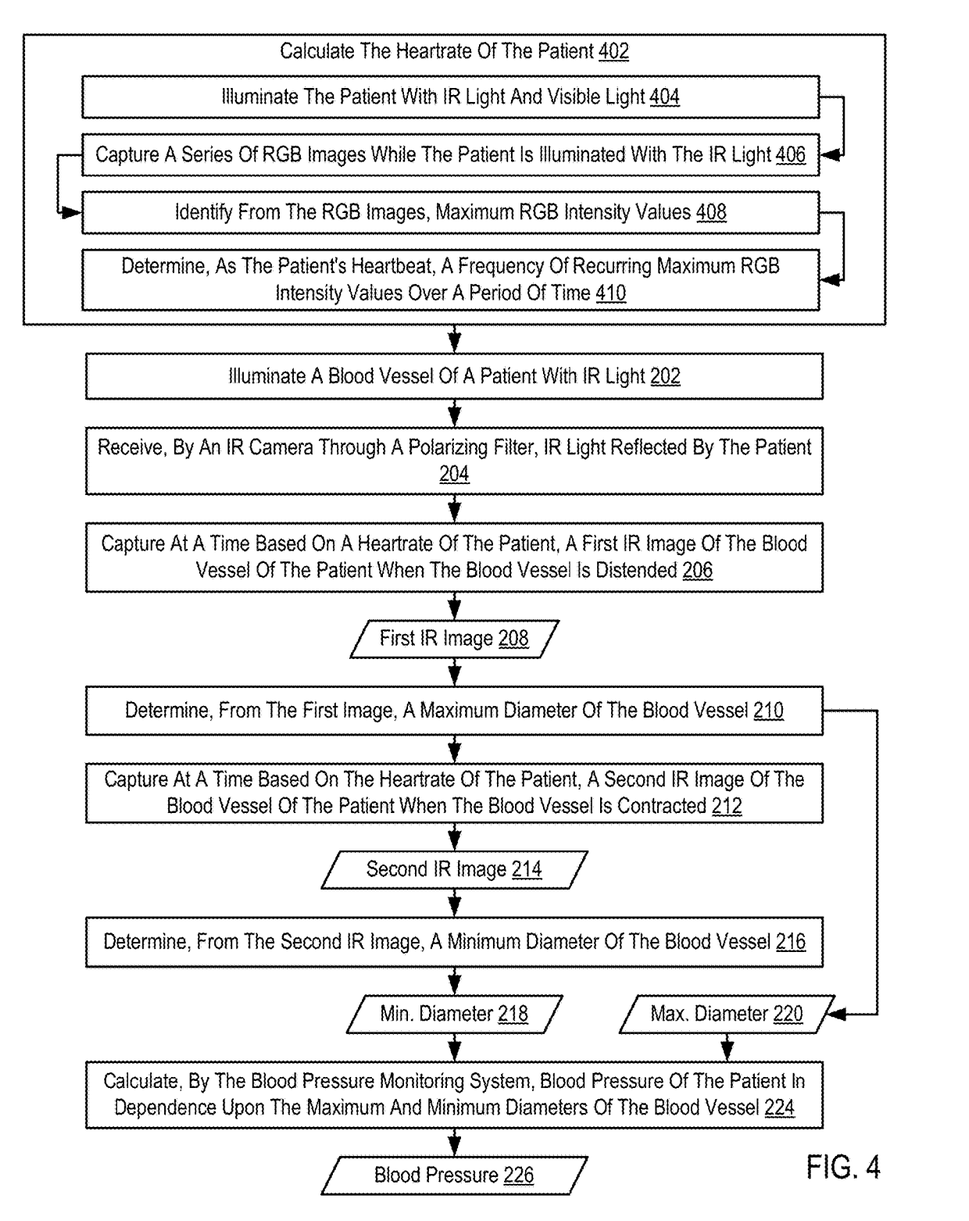
FIG. 4 sets forth a flow chart illustrating a further exemplary method for contactless blood pressure monitoring of a patient according to embodiments of the present invention that includes calculating the heartrate of the patient.

The method of FIG. 4 is similar to the method of FIG. 2, in that the method of FIG. 4 also includes illuminating (202) a blood vessel of a patient with infrared IR light; receiving (204) IR light reflected by the patient; capturing (206) at a time based on a heartrate of the patient a first IR image (208) of the blood vessel of the patient when the blood vessel is distended; determining (210) a maximum diameter (220) of the blood vessel; capturing (212) at a time based on the heartrate of the patient a second IR image (214) of the blood vessel of the patient when the blood vessel is contracted; determining (216) a minimum diameter (220) of the blood vessel; and calculating (224) blood pressure (226) of the patient in dependence upon the maximum and minimum diameters of the blood vessel.

The method of FIG. 4 differs from the method of FIG. 2, however, in that the method of FIG. 4 includes calculating (402) the heartrate of the patient. In the method of FIG. 4, calculating (402) the heartrate of the patient is carried out by: illuminating (404) the patient with IR light and visible light; capturing (406) a series of RGBa ('Red, Green, Blue, Alpha') images while the patient is illuminated with the IR light; identifying (408) from the RGBa images, maximum RGBa intensity values; and determining (410), as the patient's heartbeat, a frequency of recurring maximum RGBa intensity values over a period of time.

When the heart beats, blood flows more quickly through the vessel, and the vessel distends. Upon doing so, the color of the vessel varies. The variation is periodic (or semi-periodic) based on the regular periodic heart beat of the patient. As such, the periodicity, or frequency, of the variance of the color may be utilized as the heartbeat.

Each image in the series of images includes a plurality of pixels. Each pixel is defined by intensity values for red, intensity values for green, and intensity values for blue. As the color of the vessel varies, the pixel in each image varies in intensity values. As such, identifying (408) maximum RGBa intensity values from the images may be carried out in a variety of ways. In one example, the blood pressure monitoring system may calculate for each of a number of pixels and for each color, average intensity values. The blood pressure monitoring may then calculate a score based on the sum of the average intensity values of the colors and compare those sums to sums of other images in the series. Those having the highest intensity values within a range of one another may be determined to be images containing maximum RGBa intensity values.

Not only may the heartrate of the patient be calculated for later use in capturing IR images for blood pressure calculation, but the heartrate may be a diagnostic provided to the patient or doctor.

Figure 5:
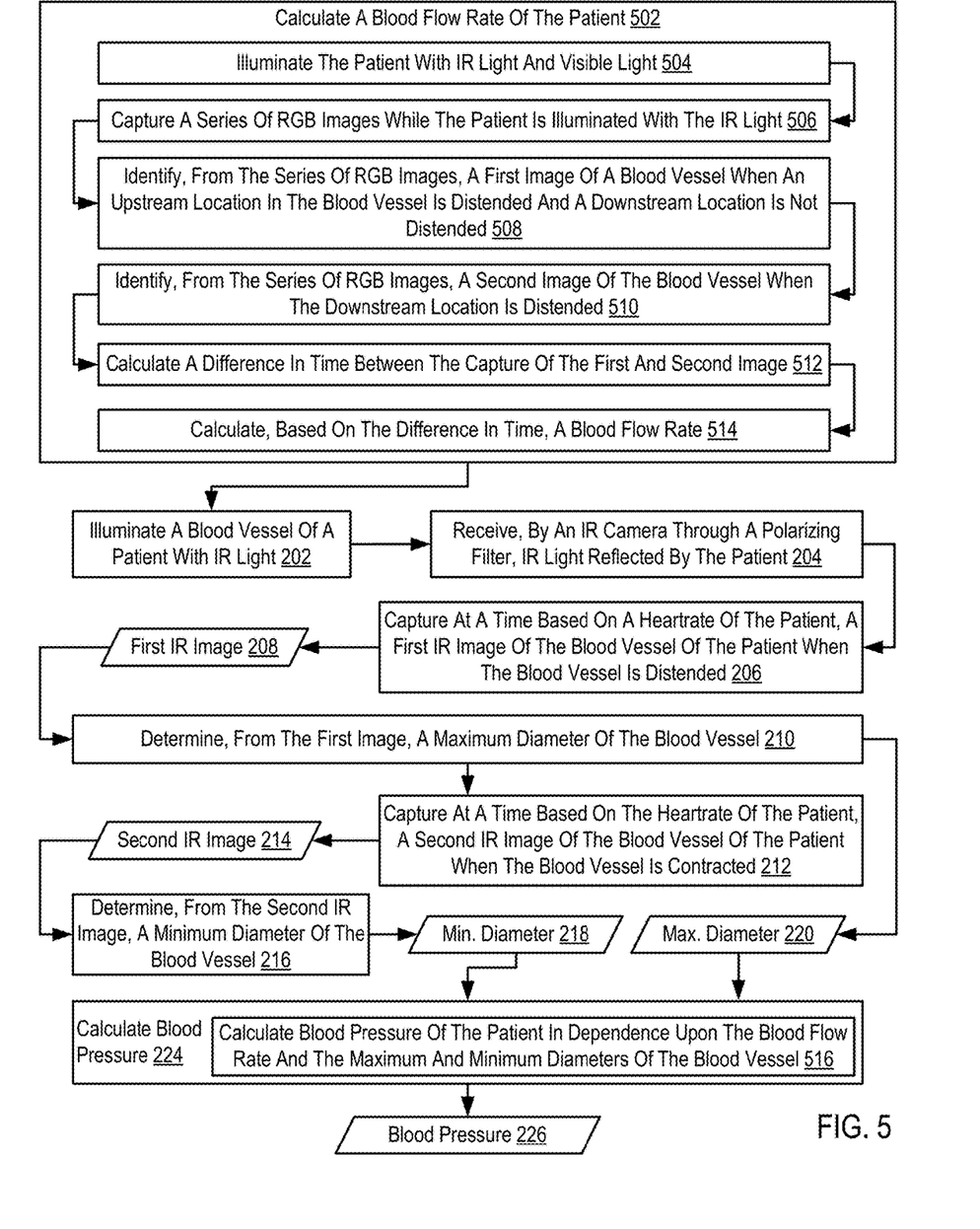
FIG. 5 sets forth a flow chart illustrating a further exemplary method for contactless blood pressure monitoring of a patient according to embodiments of the present invention that includes calculating the heartrate of the patient.

For further explanation, the method of FIG. 5 sets forth a flow chart illustrating a further exemplary method for contactless blood pressure monitoring of a patient according to embodiments of the present invention that includes calculating the heartrate of the patient. The method of FIG. 5 is similar to the method of FIG. 2, in that the method of FIG. 5 also includes illuminating (202) a blood vessel of a patient with infrared IR light; receiving (204) IR light reflected by the patient; capturing (206) at a time based on a heartrate of the patient a first IR image (208) of the blood vessel of the patient when the blood vessel is distended; determining (210) a maximum diameter (220) of the blood vessel; capturing (212) at a time based on the heartrate of the patient a second IR image (214) of the blood vessel of the patient when the blood vessel is contracted; determining (216) a minimum diameter (220) of the blood vessel; and calculating (224) blood pressure (226) of the patient in dependence upon the maximum and minimum diameters of the blood vessel.

The method of FIG. 5 differs from the method of FIG. 2, however, in that the method of FIG. 5 includes calculating (502) a blood flow rate of the patient. In the method of FIG. 5, calculating the blood flow rate of the patient is carried out by: illuminating (504) the patient with IR light and visible light; capturing (506) a series of RGBa images while the patient is illuminated with the IR light; identifying (508), from the series of RGBa images, a first image of a blood vessel when an upstream location in the blood vessel is distended and a downstream location is not distended; identifying (510), from the series of RGBa images, a second image of the blood vessel when the downstream location is distended; calculating (512) a difference in time between the capture of the first and second image; and calculating (514), based on the difference in time, a blood flow rate.

Blood flow rate may be determined by the time it takes for blood to flow from one point, an upstream location, to a second point in the blood vessel, a downstream location. The blood pressure monitoring system may be configured or calculate a distance between the upstream and downstream location, then identify in the images when the blood flows through each location. The blood pressure monitoring may identify a time when the blood flows through a location as the time at which the vessel distends at that location. That is, at a first time, the blood flows through the upstream location, distending the vessel at that location. Later, at a second time, the blood flows through the downstream location distending the vessel at that location. The ratio of the difference in times between the two distensions and the distance between the two locations is the blood flow rate.

As mentioned above, the blood flow rate may be utilized in the calculation of blood pressure. To that end, calculating (224) blood pressure of the patient may be carried out by calculating (516) blood pressure of the patient in dependence upon the blood flow rate and the maximum and minimum diameters of the blood vessel.

Figure 6:
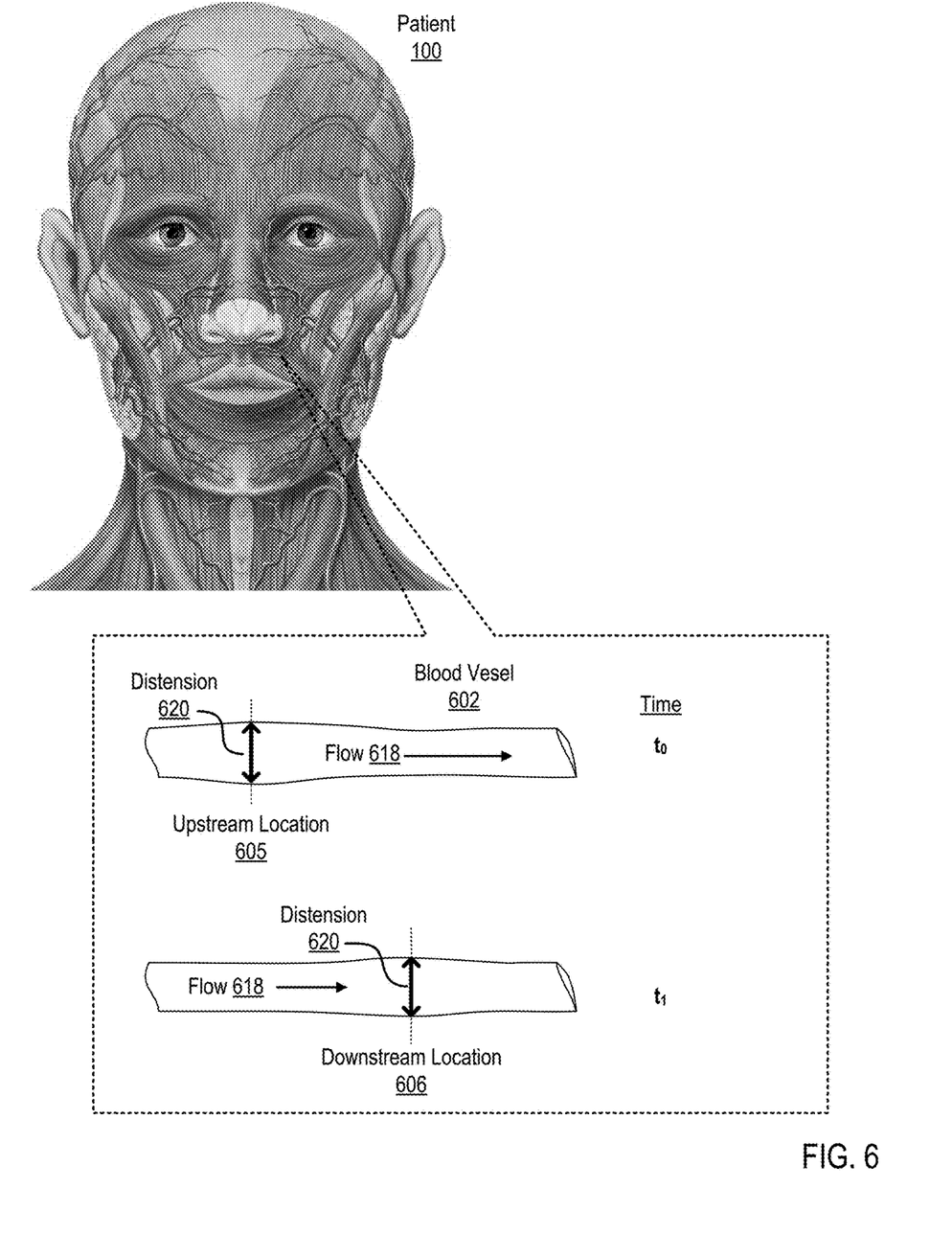
FIG. 6 sets forth another diagram of a blood vessel of a patient.

For further explanation, FIG. 6 sets forth another diagram of a vessel of a patient. One vessel (602) of the patient is blown up for clarity. The vessel (602) is shown at two times: $t_0$ in which an upstream location (605) is distended (620) due to blood flow (618) and $t_1$ in which the downstream location (606) of the vessel is distended due to blood flow. Over a period of time, while the patient is illuminated with IR light, the blood pressure monitoring system may capture a series of IR images that includes the vessel at $t_0$ and $t_1$. From the images the blood pressure monitoring system may identify the image containing the upstream location distended and the image containing the downstream location distended. The blood pressure monitoring system may then calculate or determine the time between the capture of those images. Finally, the blood pressure monitoring system may divide the difference in time by the distance between the two locations (605, 606).

Figure 7:
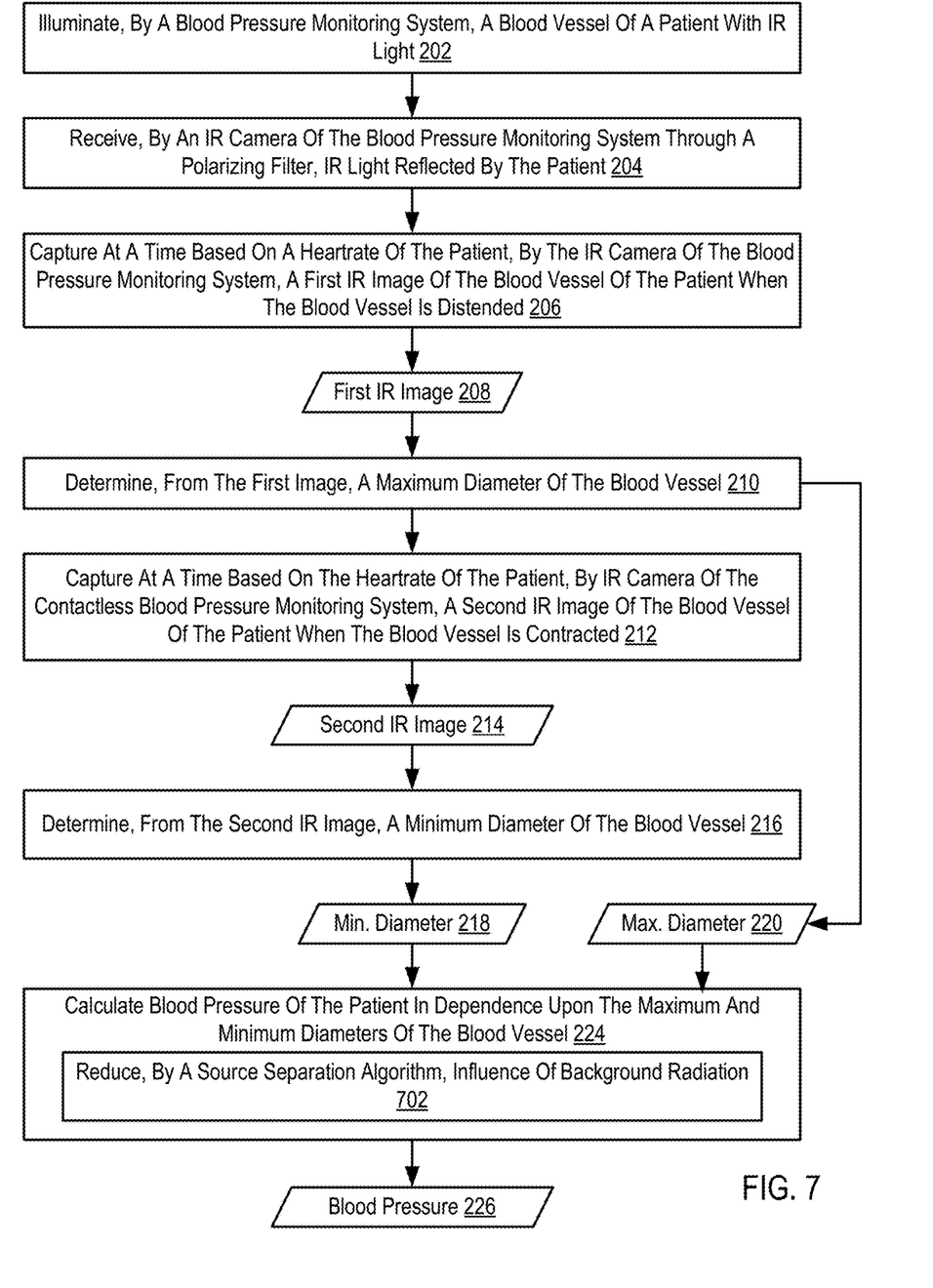
FIG. 7 sets forth a flow chart illustrating a further exemplary method for contactless blood pressure monitoring of a patient according to embodiments of the present invention that includes calculating the heartrate of the patient.

For further explanation, the method of FIG. 7 sets forth a flow chart illustrating a further exemplary method for contactless blood pressure monitoring of a patient according to embodiments of the present invention that includes calculating the heartrate of the patient. The method of FIG. 7 is similar to the method of FIG. 2, in that the method of FIG. 7 also includes illuminating (202) a blood vessel of a patient with infrared IR light; receiving (204) IR light reflected by the patient; capturing (206) at a time based on a heartrate of the patient a first IR image (208) of the blood vessel of the patient when the blood vessel is distended; determining (210) a maximum diameter (220) of the blood vessel; capturing (212) at a time based on the heartrate of the patient a second IR image (214) of the blood vessel of the patient when the blood vessel is contracted; determining (216) a minimum diameter (220) of the blood vessel; and calculating (224) blood pressure (226) of the patient in dependence upon the maximum and minimum diameters of the blood vessel.

The method of FIG. 7 differs from the method of FIG. 2 in that in the method of FIG. 7, calculating (224) the blood pressure (226) of the patient also includes reducing (702), by a source separation algorithm, influence of background radiation. In some embodiments, stray, ambient, or background radiation may reach the IR camera of the blood pressure monitoring system. Such background radiation may include IR and RGBa sources other than those controlled by the blood pressure monitoring system. To that end, a source separation algorithm may be applied to filter some or all of the background radiation from the image data provided by the camera. A source separation algorithm attempts to identify distinct components that have been combined and remove all but the desired component. To aid the source separation algorithm, the camera may capture images when no patient is present to identify background radiation that is present and likely to be captured by the camera. Then, when applying the source separation algorithm the previously identified background radiation may be taken into account when removing components that may be undesirable for blood pressure monitoring calculations. Further, multiple known light sources may be projected on the user to limit the amount of stray radiation that can be received by the camera.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A method of contactless blood pressure monitoring of a patient by a blood pressure monitoring system, the method comprising:
    illuminating a face of the patient including at least one blood vessel with infrared (IR') light with an IR light source, wherein the blood pressure monitoring system comprises an IR camera, the IR light source, a polarizing filter, and a computer processor
    receiving, by the IR camera through the polarizing filter, IR light reflected by the patient;

capturing during a first time period, by the IR camera, a plurality of first IR images of at least one region of the face of the patient including the at least one blood vessel;

selecting, based on a heartrate of the patient, from the plurality of first IR images, a first IR image including the at least one blood vessel when the at least one blood vessel is distended;

determining, by the blood pressure monitoring system from the first IR image, a maximum diameter of the at least one blood vessel, wherein the determining comprises measuring, from the first IR image, a distance between points on the at least one blood vessel;

capturing during a second time period, by the IR camera, a plurality of second IR images of at least one region of the face of the patient including the at least one blood vessel;

selecting, based on a heartrate of the patient, from the plurality of second IR images, a second IR image including the at least one blood vessel when the at least one blood vessel is contracted;

determining, by the blood pressure monitoring system from the second IR image, a minimum diameter of the at least one blood vessel, wherein the determining comprises measuring, from the second IR image, a distance between points on the at least one blood vessel;

calculating, by the computer processor of the blood pressure monitoring system, blood pressure of the patient in dependence upon the maximum and minimum diameters of the at least one blood vessel and blood flow rate; and providing, by the blood pressure monitoring system, the calculated blood pressure to a user selected from a group consisting of the patient and a physician.

2. The method of claim 1 further comprising calculating the heartrate of the patient, wherein the blood pressure monitoring system comprises an RGB camera, including:
wherein illuminating further comprises illuminating the face of the patient with the IR light and visible light;
capturing a series of RGBa ('Red, Green, Blue, Alpha') images while the patient is illuminated with the IR light;
identifying from the RGBa images, maximum RGBa intensity values; and
determining, as the patient's heartrate, a frequency of recurring maximum RGBa intensity values over a period of time.

3. The method of claim 1 further comprises calculating a blood flow rate of the patient, wherein the blood pressure monitoring system comprises an RGB camera, including:
wherein illuminating further comprises illuminating the face of the patient with the IR light and visible light;
capturing a series of RGBa ('Red, Green, Blue, Alpha') images while the patient is illuminated with the IR light;
identifying, from the series of RGBa images, a first image of a blood vessel when an upstream location in the blood vessel is distended and a downstream location is not distended;
identifying, from the series of RGBa images, a second image of the blood vessel when the downstream location is distended;
calculating a difference in time between the capture of the first and second image; and
calculating, based on the difference in time, a blood flow rate.

4. The method of claim 3 wherein calculating blood pressure of the patient further comprises calculating blood pressure of the patient in dependence upon the blood flow rate and the maximum and minimum diameters of the at least one blood vessel.

5. The method of claim 1 wherein calculating the blood pressure of the patient further comprises reducing, by a source separation algorithm, influence of background radiation.

6. The method of claim 1, wherein the calculation of blood pressure is updated periodically while the patient is present.

7. An apparatus for contactless blood pressure monitoring of a patient, the apparatus comprising:
a computer processor, an infrared (IR') camera, an IR light source, a polarizing filter, and a computer memory operatively coupled to the computer processor, wherein the computer memory has disposed within it computer program instructions that, when executed by the computer processor, cause the apparatus to carry out the steps of:
illuminating a face of the patient including at least one blood vessel with IR light with the IR light source;
receiving, by the IR camera through the polarizing filter, IR light reflected by the patient;
capturing during a first time period, by the IR camera, a plurality of first IR images of at least one region of the face of the patient including the at least one blood vessel;
selecting, based on a heartrate of the patient, from the plurality of first IR images, a first IR image including the at least one blood vessel when the at least one blood vessel is distended;
determining, by the blood pressure monitoring system from the first IR image, a maximum diameter of the at least one blood vessel, wherein the determining comprises measuring, from the first IR image, a distance between points on the at least one blood vessel;
capturing during a second time period, by the IR camera, a plurality of second IR images of at least one region of the face of the patient including the at least one blood vessel;
selecting, based on a heartrate of the patient, from the plurality of second IR images, a second IR image including the at least one blood vessel when the at least one blood vessel is contracted;
determining, from the second IR image, a minimum diameter of the at least one blood vessel, wherein the determining comprises measuring, from the second IR image, a distance between points on the at least one blood vessel;
calculating blood pressure of the patient in dependence upon the maximum and minimum diameters of the at least one blood vessel and blood flow rate; and
providing the calculated blood pressure to a user selected from a group consisting of the patient and a physician.

8. The apparatus of claim 7, wherein the apparatus further comprises an RGB camera, and wherein the computer memory has disposed within it further computer program instructions that, when executed by the computer processor, cause the apparatus to carry out the step of calculating the heartrate of the patient including:
wherein illuminating further comprises illuminating the face of the patient with the IR light and visible light;
capturing a series of RGBa ('Red, Green, Blue, Alpha') images while the patient is illuminated with the IR light;

identifying from the RGBa images, maximum RGBa intensity values; and
determining, as the patient's heartrate, a frequency of recurring maximum RGBa intensity values over a period of time.

9. The apparatus of claim 7, wherein the apparatus further comprises an RGB camera, and wherein the computer memory has disposed within it further computer program instructions that, when executed by the computer processor, cause the apparatus to carry out the step of calculating a blood flow rate of the patient, including:
wherein illuminating further comprises illuminating the face of the patient with the IR light and visible light;
capturing a series of RGBa ('Red, Green, Blue, Alpha') images while the patient is illuminated with the IR light;
identifying, from the series of RGBa images, a first image of a blood vessel when an upstream location in the blood vessel is distended and a downstream location is not distended;
identifying, from the series of RGBa images, a second image of the blood vessel when the downstream location is distended;
calculating a difference in time between the capture of the first and second image; and
calculating, based on the difference in time, a blood flow rate.

10. The apparatus of claim 9 wherein calculating blood pressure of the patient further comprises calculating blood pressure of the patient in dependence upon the blood flow rate and the maximum and minimum diameters of the at least one blood vessel.

11. The apparatus of claim 7 wherein calculating the blood pressure of the patient further comprises reducing, by a source separation algorithm, influence of background radiation.

12. The apparatus of claim 7, wherein the calculation of blood pressure is updated periodically while the patient is present.

13. A computer program product for contactless blood pressure monitoring of a patient, the computer program product disposed upon a non-transitory computer readable medium, the computer program product comprising computer program instructions that, when executed by a computer processor of a blood pressure monitoring system, cause the blood pressure monitoring system to carry out the steps of:
illuminating a face of the patient including at least one blood vessel with infrared (IR') light with an IR light source, wherein the blood pressure monitoring system further comprises an IR camera, the IR light source, and a polarizing filter;
receiving, by the IR camera through the polarizing filter, IR light reflected by the patient;
capturing during a first time period, by the IR camera, a plurality of first IR images of at least one region of the face of the patient including the at least one blood vessel;
selecting, based on a heartrate of the patient, from the plurality of first IR images, a first IR image including the at least one blood vessel when the at least one blood vessel is distended;
determining, by the blood pressure monitoring system from the first IR image, a maximum diameter of the at least one blood vessel, wherein the determining comprises measuring, from the first IR image, a distance between points on the at least one blood vessel;
capturing during a second time period, by the IR camera, a plurality of second IR images of at least one region of the face of the patient including the at least one blood vessel;
selecting, based on a heartrate of the patient, from the plurality of second IR images, a second IR image including the at least one blood vessel when the at least one blood vessel is contracted;
determining, by the blood pressure monitoring system from the second IR image, a minimum diameter of the at least one blood vessel, wherein the determining comprises measuring, from the second IR image, a distance between points on the at least one blood vessel;
calculating, by the computer processor of the blood pressure monitoring system, blood pressure of the patient in dependence upon the maximum and minimum diameters of the at least one blood vessel and blood flow rate; and
providing, by the blood pressure monitoring system, the calculated blood pressure to a user selected from a group consisting of the patient and a physician.

14. The computer program product of claim 13 further comprising computer program instructions that, when executed, cause the computer to carry out the step of calculating the heartrate of the patient including:
wherein illuminating further comprises illuminating the face of the patient with the IR light and visible light;
capturing a series of RGBa ('Red, Green, Blue, Alpha') images while the patient is illuminated with the IR light, wherein the blood pressure monitoring system comprises an RGB camera, and;
identifying from the RGBa images, maximum RGBa intensity values; and
determining, as the patient's heartrate, a frequency of recurring maximum RGBa intensity values over a period of time.

15. The computer program product of claim 13 further comprising computer program instructions that, when executed, cause the computer to carry out the step of calculating a blood flow rate of the patient, including:
wherein illuminating further comprises illuminating the face of the patient with the IR light and visible light;
capturing a series of RGBa ('Red, Green, Blue, Alpha') images while the patient is illuminated with the IR light, wherein the blood pressure monitoring system comprises an RGB camera, and;
identifying, from the series of RGBa images, a first image of a blood vessel when an upstream location in the blood vessel is distended and a downstream location is not distended;
identifying, from the series of RGBa images, a second image of the blood vessel when the downstream location is distended;
calculating a difference in time between the capture of the first and second image; and
calculating, based on the difference in time, a blood flow rate.

16. The computer program product of claim 15 wherein calculating blood pressure of the patient further comprises calculating blood pressure of the patient in dependence upon the blood flow rate and the maximum and minimum diameters of the at least one blood vessel.

17. The computer program product of claim 13 wherein calculating the blood pressure of the patient further comprises reducing, by a source separation algorithm, influence of background radiation.

18. The computer program product of claim 13, wherein the calculation of blood pressure is updated periodically while the patient is present.

\* \* \* \* \*